United States Patent
Schneider et al.

[11] Patent Number: 5,855,554
[45] Date of Patent: Jan. 5, 1999

[54] IMAGE GUIDED BREAST LESION LOCALIZATION DEVICE

[75] Inventors: Erika Schneider, Rexford; Kenneth William Rohling; Randy Otto John Giaquinto, both of Burnt Hills, all of N.Y.

[73] Assignee: General Electric Company, Schenectady, N.Y.

[21] Appl. No.: 819,430

[22] Filed: Mar. 17, 1997

[51] Int. Cl.⁶ ................................................ A61B 06/04
[52] U.S. Cl. ........................... 600/407; 378/37; 606/130
[58] Field of Search ............................ 128/653.1, 653.2, 128/653.5, 915; 378/37; 606/130; 600/407, 410, 421, 437

[56] References Cited

U.S. PATENT DOCUMENTS

| | | |
|---|---|---|
| 4,580,561 | 4/1986 | Williamson . |
| 5,105,457 | 4/1992 | Glassman .................................. 378/163 |
| 5,289,520 | 2/1994 | Pellegrino et al. ......................... 378/37 |
| 5,320,111 | 6/1994 | Livingston ............................... 128/754 |
| 5,415,169 | 5/1995 | Siczek et al. .......................... 128/653.1 |
| 5,437,280 | 8/1995 | Hussman ............................... 128/653.2 |
| 5,451,789 | 9/1995 | Wong et al. ......................... 250/363.03 |
| 5,534,778 | 7/1996 | Loos et al. ............................... 324/318 |
| 5,564,438 | 10/1996 | Merchant ................................. 128/845 |
| 5,595,177 | 1/1997 | Mena et al. ........................... 128/653.1 |
| 5,609,152 | 3/1997 | Pellegrino et al. ................... 128/653.1 |

Primary Examiner—Marvin M. Lateef
Assistant Examiner—Shawna J. Shaw
Attorney, Agent, or Firm—Lawrence P. Zale; Marvin Snyder

[57] ABSTRACT

A novel breast localization and biopsy system employs a chest support for holding the patient in a slightly rotated (20°–30°) prone position allowing the breast tissue hang downward and fit through an opening in the chest support, while holding the other breast against the subject away from the imaging region. A pair of support plates compress the breast tissue. At least one of the support plates has a grid with reference markers for localization and windows allowing a physician access to the breast tissue. A thick biopsy plate with a plurality of holes at marked positions fits into one of the grid openings and guides an interventional device, such a biopsy needle, into a desired location in a lesion. In an alternative embodiment, both breasts fit through the chest support. There are two stabilization plate assemblies, one for each breast and two medical imaging sources. Each source points from the lateral to medial support plate to accomplish imaging of both breasts simultaneously.

17 Claims, 4 Drawing Sheets

IMAGE GUIDED BREAST LESION LOCALIZATION DEVICE

BACKGROUND OF THE INVENTION

1. Scope of the Invention

The present invention relates to tissue localization in a living subject.

2. Related Prior Art

Typically, it is necessary to determine if a lesion is present within breast tissue of a living subject prior to treating it. To locate a lesion within the breast, tissue is imaged with a reference frame having reference markers which show up on the image. The lesion location relative to the markers is identified. A corresponding external location on the subject's breast is then determined relative to reference frame. This external location may then used to target the lesion in a medical procedure.

The breast tissue should remain fixed between the imaging step and the localization or the medical procedure. If the breast tissue moves after imaging and before localization, the location relative to the reference markers will apply to different tissue than the lesion. Therefore, the breast must be immobilized.

Once the proper location of the lesion is determined, it is often necessary to insert an invasive device into the lesion as part of the medical procedure. One such procedure is to biopsy the lesion with a biopsy needle. Since the lesion material is sometimes has a higher density than surrounding breast tissue, it is not always easy to insert a biopsy device into the lesion.

Prior art devices for localization, biopsy and treatment of breast lesions provide support for the breast tissue and/or guides to insert an interventional device. However, many of these devices suffer a lack of access to the breast tissue. Sometimes it is necessary to use a scalpel to "nick" or cut the skin in order to provide biopsy or treatment access to the lesion. The prior art devices do not provide both access for a scalpel, and accurate spatial targeting simultaneously.

It is necessary to minimize the distance (the amount of tissue affected) traveled by the biopsy or interventional device. Therefore, it may also be necessary to access the lesion from either the medial or lateral side of the breast. Many prior art devices do not provide both medial and lateral access to the breast tissue.

In addition to these problems, many of the prior art devices do not pull the breast tissue away from the chest wall and access the entire breast, including most of the axilla, for localization, biopsy, treatment as well as imaging.

Currently there is a need for a breast lesion localization device which images the entire breast, guides an interventional device into the lesion accurately, and allows a Physician greater access to breast tissue.

SUMMARY OF THE INVENTION

A tissue localization system intended for use in a medical imaging device for localization, biopsy, and treatment of breast lesions employs a chest support for supporting said subject's chest when said subject is in a prone position. The support has at least one opening for receiving a breast of the subject, allowing the breast to fit through the opening, while flattening the subject's other breast against said subject's chest, when imaging only a single breast. A first stabilization plate is constructed of a material which is substantially translucent to a medical imaging device, for stabilizing one side of the breast hanging down through the opening. The stabilization plate is constructed of a grid having a plurality of windows large enough to receive a scalpel and sufficiently small such that the breast tissue does not significantly bulge.

A second stabilization plate constructed of a material substantially translucent to said medical imaging device is used for stabilizing the other side of the breast. Detectors for a medical imaging system can be located in one or both stabilization plates, depending upon the embodiment. The stabilization plates are moved toward each other compressing the breast between the stabilization plates.

A plurality of reference markers which show up on the medical image are located at known locations on the stabilization plates.

A biopsy plate having a size and shape to fit within one of the windows of the grid, is positioned within a selected window closest to the lesion (as located from the image relative to the reference markers). The biopsy plate has a substantial thickness with a plurality of holes traveling through it. Each of these holes may be used for guiding a biopsy needle or localization needle or treatment device into the breast of the subject.

OBJECTS OF THE INVENTION

An object of the present invention is to provide a system which accurately and reliably localizes a desired tissue or location within a living subject by imaging.

Another object of the present invention is to localize lesions in a subject's breast by imaging, and guide an interventional device into the lesion without having to reposition the subject.

Another object of the present invention is to localize lesions in a subject's breast by imaging, and accurately insert an interventional device into the lesion.

BRIEF DESCRIPTION OF THE DRAWINGS

The features of the invention believed to be novel are set forth with particularity in the appended claims. The invention itself, however, both as to organization and method of operation, together with further objects and advantages thereof, may be best understood by reference to the following description taken in conjunction with the accompanying drawings in which:

DETAILED DESCRIPTION OF THE INVENTION

Figure 1:
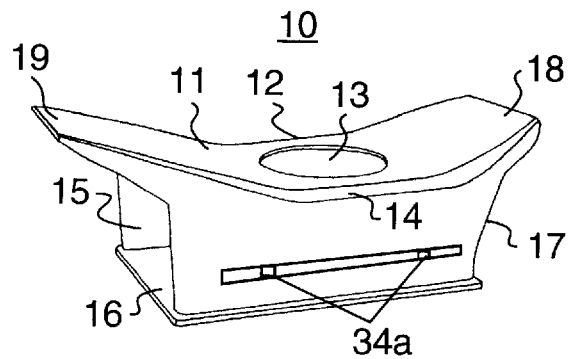
FIG. 1 is a perspective view of a chest support for image-guided breast lesion localization and treatment according to the present invention.
Figure 3:
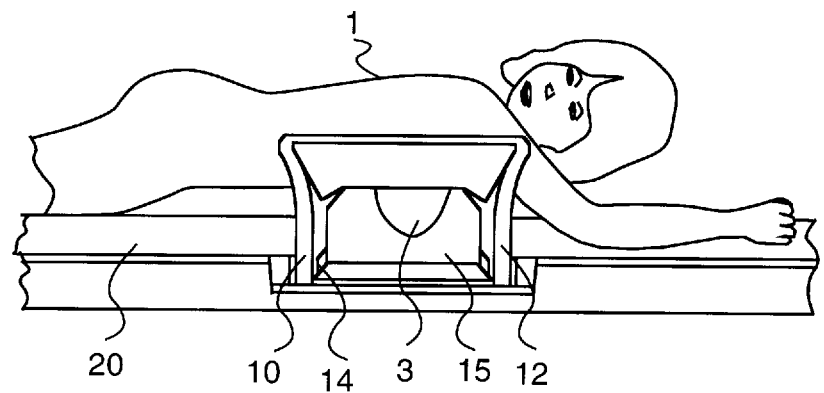
FIG. 3 shows a subject positioned as they would appear during localization and treatment on a table fitted with apparatus according to the present invention.
Figure 4:
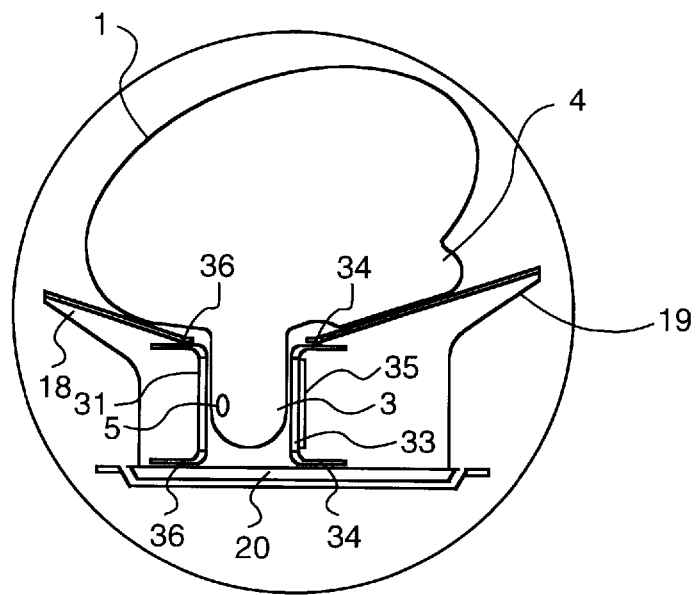
FIG. 4 is a cross sectional view of a subject as the subject would appear during an interventional procedure with the present invention.

In FIG. 1, a chest support 10 according to the present invention is shown in perspective view. Chest support 10 has a top surface 11 having a breast opening 13 for receiving a breast of the subject intended to be imaged. In FIG. 3 and 4, as subject 1 is positioned in the prone position rotated 20°–30° such that subject's breast 3, and axilla pass through breast opening 13 hanging downward by the force of gravity. Since gravity acts on breast 3 it is pulled away from chest wall of subject 1 allowing greater access for imaging and treatment. Chest support 10 may be retrofitted to existing tables of medical imaging devices such as magnetic resonance (MR), X-ray, ultrasound or computer tomography (CAT) imaging devices.

In the preferred embodiment, the shape of top surface 11 of chest support 10 should be curved to rotate the torso of the subject downward 20°–30°. This rotation allows the complete breast (especially lateral side) and a significant portion of axilla to be introduced into the opening 13. Chest support 10 may also be designed to have a first side 12 substantially shaped like a second side 14 such that the support may be rotated around to image the other breast. For imaging a single breast, chest support 10 has right side 18 left side 19 asymmetry to support the non-imaged breast 4. Also note that chest support 10 has openings 15 and 17 on both sides allowing access to the medial and lateral sides of breast 3.

Chest support 10 also has a base 16 which is useful for structural support, but also serves to collect, and contain fluids during a procedure.

Figure 2:
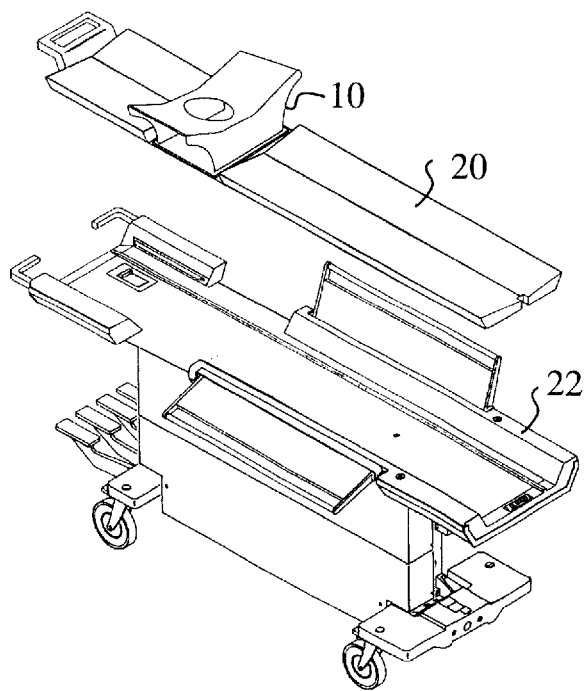
FIG. 2 shows a perspective illustration of the chest support of FIG. 1 retrofitted to an existing medical imaging device table and associated apparatus.

FIG. 2 shows a perspective illustration of the chest support of FIG. 1 retrofitted to an existing medical imaging device table 20 and associated apparatus 22.

FIG. 3 shows a subject 1 during localization and treatment on table 20 fitted with apparatus according to the present invention.

The patient is placed prone, feet first, at a 20 to 30 degree rotation with medial-lateral (ML) stabilization of the breast tissue. This patient position allows access both medial and lateral aspects of the breast, and minimizes the needle trajectory. In addition, this positioning uses gravity to pull the breast tissue (including part of the axillary tail) away from the chest wall, thus maximizing the amount of tissue available for imaging and biopsy. The superior-inferior symmetry of the positioning device enables it to be used for biopsy of either the right or the left breast. Access for needle localization or biopsy is achieved from either the medial or lateral side.

FIG. 4 is a cross sectional view of a subject as the subject would appear during an imaging or interventional procedure with the present invention.

Immobilization of the breast tissue 3 and lesion 5 is achieved with two parallel, translucent stabilization plates 31, 33 placed medially and laterally. Whether a medial or lateral approach is needed for lesion localization should be decided in advance of the procedure on the basis of prior diagnostic exams.

The breast side through which the lesion will not be localized or biopsied will have a smooth vertical stabilization plate containing an imaging detector 35, such as an MR coil, for MR imaging, an acoustic reflecting plate for ultrasound imaging, a scintillator array, for X-ray and CT imaging, collects imaging data from subject 1. Since the detector is so close to the tissue being imaged, the signal-to-noise ratio is large, producing higher-quality images that those with detectors placed at locations further from breast tissue 3.

The medial stabilization plate 33 should be secured first. Plate 33 is preferred to be positioned using side guides 34a, such that plate 33 is substantially parallel to plate 31 and it is locked into place against breast tissue 3. Horizontal supports 34, 36 structurally allow side guides to slide within chest support 10, and to support the chest to prevent pinching tissue when plate 33 is retracted. Breast 3 should only be slightly displaced by the plate from its natural, pendulent position.

From the opposite breast side, plate 31 is placed into guide slots of side guides 34a such that it is substantially perpendicular to table 20 and parallel to plate 33. Plate 31 is moved toward plate 33, compressing the breast, such that the breast tissue 3 and lesion 5 are stabilized. The amount of compression necessary for stabilization of the breast tissue for MR imaging is significantly lower than that required for X-Ray mammography and should not be painful. Subject 1 should be able to lay comfortably, without moving, for 45 minutes, about the time required for a typical procedure.

Figure 5:
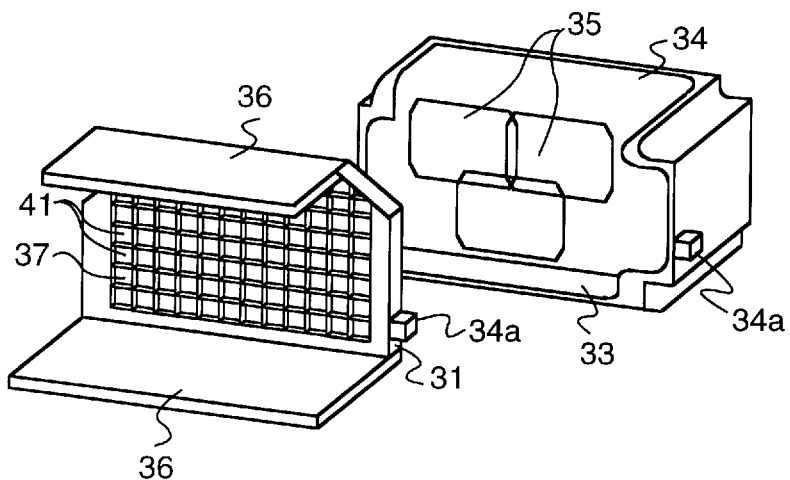
FIG. 5 is a more detailed view of stabilization plates shown in FIG. 4.

FIG. 5 is a more detailed view of stabilization plates shown in FIG. 4. Imaging detector 35, such as an MR coil, for MR imaging, a scintillator array, such as in X-ray and CT imaging collects imaging data from subject 1. Detector 35 can be located in either or both stabilization plates 31, 33 (as explained in an alternative embodiment below). For MR imaging, the MR coils have been optimized for coverage and signal-to noise (SNR) over the range of loading conditions expected for the MR-accessible population. To accommodate a wide distribution of patients, different size detectors 35 may be used for different sized women. For different applications, such as needle localization, biopsy, or treatment, several biopsy plates 39 can be made with different size holes 43.

Figure 6:
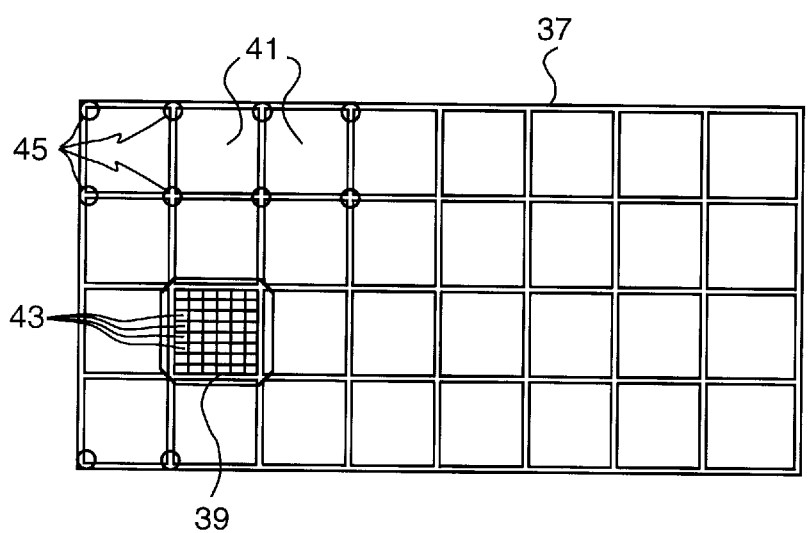
FIG. 6 is an illustration of one embodiment of a stabilization plate shown in FIG. 5 having an attached biopsy plate, according to the present invention.

FIG. 6 is a more detailed view of one of the stabilization plates shown in FIG. 4 having an attached biopsy plate, according to the present invention. Stabilization plate 31 consists of a two piece device: a grid 37 and a biopsy plate 39.

Stabilization plate 31 has windows 41. A typical window size would be 2.5 centimeters by 2.5 centimeters. A grid 37 surrounds each of these windows. Reference markers 45 are employed in grid 37 which correspond to the type of imaging being performed. Reference markers may also be attached to a separate removable plate connected to one o the stabilization plates. Where x-ray imaging it would be x-ray opaque markers, for MR imaging, it would be MR active material, etc. These reference markers show up on the image along with the lesion. They are then used to determine the location of the lesion relative to reference markers 45 and grid 37.

Using only a stabilization plate 31 with large windows 41 would cause breast tissue to bulge through the windows thereby not producing a flat surface in which to insert an interventional device. This bulge will make accurate targeting difficult while also making it more difficult to pierce the lesion with an interventional device. Therefore a greater amount of support is required and is achieved with stabilization plate 31 shown in FIG. 6.

A biopsy plate 39 containing an array of holes, is positioned in the desired window 41. Biopsy plate 39 has a significant thickness (which is perpendicular to the plane of the paper shown in FIG. 6), which guides a biopsy needle in a straight direction into a lesion. Biopsy plate may also have reference markers 46 to further refine the location to insert an interventional device. Local biopsy plate 39 may be removed and inserted into any of the windows 41.

Needle positioning by biopsy plate 39 occurs substantially in a y-z axis (the stabilization plate being substantially in the y-z plane). For the last dimension (x), it may be determined from the image and the reference markers the depth the biopsy needle is to penetrate to its desired location. This may be measured by markings on the needle or interventional device.

The degree of accuracy determines the thickness T of biopsy plate 39 and hole diameter relative to the needle it is receiving. The holes 43 have a diameter difference Δd greater than the needle diameter that they receive. The angular offset from perpendicular is measured by an angle θ. Therefore, by simple geometry, to have an angular offset of θ or less, the plate thickness and hole diameter difference is defined by:

$$\tan(\theta) = \Delta d / T;$$

or for an angular accuracy of θ:

$$\theta = \tan^{-1}\{\Delta d/T\}.$$

From the angular accuracy, and a depth D of the needle penetration, the maximum linear accuracy A can be computed:

linear accuracy A=D * tan(θ);
linear accuracy A=DΔd/T.

Conversely, the maximum allowable linear accuracy allowed by the procedure can be used to determine the design parameters Δd and T.

Figure 7:
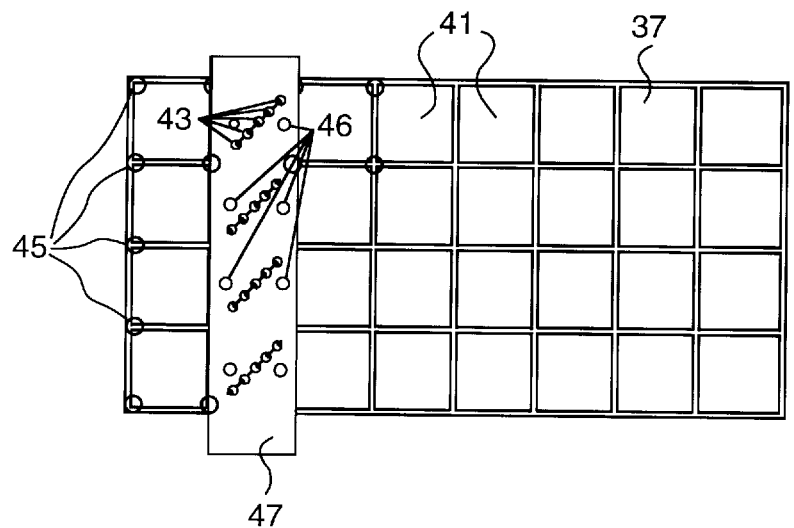
FIG. 7 is an illustration of a second embodiment of a stabilization plate as shown in FIG. 5, according to the present invention.

An alternative embodiment of the stabilization plate 31 of FIG. 5 is shown in FIG. 7. A slider 47 slides left and right on a grid 37 to a proper location, overlapping a particular window 41. This location may have been previously identified on an image relative to reference markers 46. Holes 49, which may be arranged in many different patterns, receive an interventional device, such as a biopsy needle. The pattern of holes shown in FIG. 7 is a diagonal line arrangement. Slider 47 is then used to guide the interventional device into the lesion. Use of such a slider and grid increases the achievable spatial resolution in the y-z plane.

Since windows 41 are large enough, it allows access to breast tissue 3 such that skin may be "nicked" or superficial tissue be cut away. Since some interventional devices have a large cross-section, it is desirable to first cut the skin with a scalpel. This produces a clean skin cut which heals better, has less scarring, and less chance of infection.

In an alternative embodiment, there are two stabilization plates like plate 31 either capable of receiving biopsy plate 39 for performing medical procedures from either side. Detector 35 may be incorporated into one, or both, of these plates.

Figure 8:
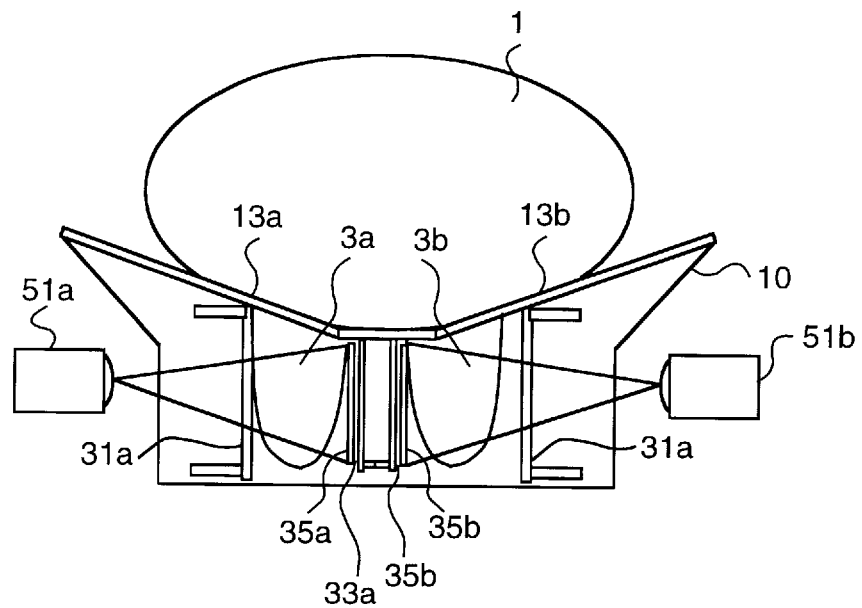
FIG. 8 is another embodiment of the present invention capable of imaging both breasts simultaneously.

In another alternative embodiment as shown in FIG. 8, chest support 10 has two openings 13a, 13b each for receiving one of the subject's breasts 3. There are also two sets of stabilization plates 31a, 33a, 31b, 33b, with detectors 35a, 35b compressing each breast 3. Two medical imaging sources 51a, 51b such as an X-ray or ultrasound source are located at the lateral sides of subject 1 with detectors 35a, 35b placed on the medial side of each breast for acquiring image data of each. This allows both breasts to be imaged, localized, and treated at the same time.

Therefore, grid 37 in combination with biopsy plate 39 provides a system for stabilizing breast 3 and allowing access to breast 3 both medial and lateral or for cutting while also guiding an interventional device into a lesion.

The present invention may also be used, but less effectively, with the subject in a standing position.

While several preferred embodiments of the novel invention has been described in detail herein, many modifications and variations will now become apparent to those skilled in the art. It is, therefore, to be understood that the appended claims are intended to cover all such modifications and variations as fall within the true spirit of the invention.

What is claimed is:

1. A tissue localization system for use with a medical imaging device for reliably identifying a specific location within a breast of a subject's chest comprising:
   a) a chest support for supporting a subject's chest when said subject is in a prone position, the support having a opening for receiving a breast of the subject, allowing the breast to fit through the opening, while flattening the subject's other breast against said subject's chest;
   b) a first stabilization plate substantially translucent to said medical imaging device, adjustably secured to the chest support, for stabilizing a side of the breast, the stabilization plate comprising:
      i. a grid having a plurality of windows large enough to receive a scalpel;
      ii. a plurality of reference markers constructed of a material imaged by the medical imaging device, located at known locations of the first stabilization plate;
      iii. a biopsy plate having a size and shape to fit within the windows of the grid, having a plurality of holes each for guiding a biopsy needle or other interventional device into the breast of the subject;
   c) a second stabilization plate substantially translucent to said medical imaging device for stabilizing a second side of the breast which may be moved and adjustable secured at a location relative to the first plate, thereby securing the breast between the stabilization plates.

2. The tissue localization system of claim 1 further comprising:
   a medical imaging detector attached to one or both of the stabilization plates, for receiving imaging information from the subject, and passing the imaging information to a medical imaging device causing it to create an image of the subject's breast.

3. The tissue localization system of claim 1 wherein the medical imaging device is a magnetic resonance (MR) imaging device and further comprising:
   an MR receive coil coupled to the MR imaging device, the coil attached to one or both of the stabilization plates, for receiving MR response signals from the subject, and passing the MR response signals to the MR imaging device causing it to create an MR image of the subject's breast.

4. The tissue localization system of claim 1 wherein the medical imaging device is a computed axial tomography (CAT) imaging device and further comprising:
   an X-ray detector coupled to the CAT imaging device, the detector attached to one or both of the stabilization plates, for receiving imaging information from the subject, and passing the imaging information to the CAT imaging device causing it to create an image of the subject's breast.

5. The tissue localization system of claim 1 wherein the medical imaging device is an X-ray imaging device and further comprising:
   an X-ray detector coupled to the imaging device, the detector attached to one or both of the stabilization plates, for receiving imaging information from the subject, and passing the imaging information to the imaging device causing it to create an image of the subject's breast.

6. A tissue localization system for use with an ultrasound imaging device for reliably identifying a specific location within a breast of a subject's chest comprising:
   a) a chest support for supporting a subject's chest when said subject is in a prone position, the support having a opening for receiving a breast of the subject, allowing the breast to fit through the opening, while flattening the subject's other breast against said subject's chest;
   b) a first stabilization plate substantially translucent to said medical imaging device, for stabilizing a side of the breast, the stabilization plate comprising:
      i. a grid having a plurality of windows large enough to receive a scalpel;
      ii. a plurality of reference markers constructed of a material imaged by the medical imaging device, located at known locations of the first stabilization plate;
      iii. a biopsy plate having a size and shape to fit within the windows of the grid, having a plurality of holes each for guiding a biopsy needle or other interventional device into the breast of the subject;
   c) a second stabilization plate substantially translucent to said medical imaging device for stabilizing a second side of the breast which may be moved and adjustably secured at a location relative to the first plate, thereby securing the breast between the stabilization plates; and
   d) an ultrasound reflector plate attached to the second stabilization plate, for reflecting ultrasound energy back to an ultrasound imaging device.

7. The tissue localization system of claim 1 wherein the biopsy plate further comprises:
   reference markers at predetermined locations for localization of the lesion on the image with respect to the biopsy plate.

8. The tissue localization system of claim 1 wherein the biopsy plate has a thickness T, and the holes have a diameter difference Δd greater than a needle being guided, selected for an angular accuracy θ off perpendicular defined by:

$\theta = \tan^{-1}\{\Delta d/T\}$.

9. The tissue localization system of claim 1 wherein the biopsy plate has a thickness T, and the holes have a diameter difference Δd greater than a needle being guided, selected for an linear accuracy A defined by:

$A = D\Delta d/T$;

where D is a desired penetration depth from the biopsy plate.

10. The tissue localization system of claim 1 wherein the chest support has a first side shaped substantially the same as a second side such that it may be rotated 180° degrees to image the subject's other breast.

11. A tissue localization system for use with a medical imaging device for reliably identifying specific locations within both breasts of a subject's chest comprising:
   a) a chest support for supporting a subject's chest when said subject is in a prone position, the support having a opening for each breast, allowing each breast to fit through the opening;
   b) a pair of lateral stabilization plates substantially translucent to a medical imaging device, adjustably secured to the chest support, for stabilizing a lateral the side of each breast, the stabilization plates comprising:
      i. a grid having a plurality of windows large enough to receive a scalpel yet hold the breast in place;
      ii. a plurality of reference markers constructed of a material imaged by the medical imaging device, located at known locations of at least one of the lateral stabilization plates;
      iii. a biopsy plate having a size and shape to fit within the windows of the grid, having a plurality of holes each for guiding a biopsy needle or other interventional device into the breast of the subject; and
   c) at least one medial stabilization plate, for stabilizing a medial side of each breast which may be moved, and adjustable secured to the chest support at a location relative to the laterally stabilization plates, thereby securing the breast between the lateral medial stabilization plate and one of the lateral stabilization plates.

12. The tissue localization system of claim 11 further comprising: a medical imaging detector, attached to the medial stabilization plate for receiving image information from each breast and providing the information to said medical imaging device.

13. The tissue localization system of claim 11 further comprising: a medical imaging detector, attached to the lateral stabilization plate for receiving image information from each breast and providing the information to said medical imaging device.

14. The tissue localization system of claim 11 further comprising:
   a medical imaging source for each breast directed at the lateral side of each breast pointing to the medial stabilization plate.

15. The tissue localization system of claim 11 wherein the biopsy plate further comprises: reference markers at predetermined locations for localization of the lesion on the image with respect to the biopsy plate.

16. The tissue localization system of claim 11 wherein the biopsy plate has a thickness T, holes have a diameter difference Δd greater than the needle being guided, selected for an angular accuracy θ off perpendicular defined by:

$\theta \tan^{-1}\{\Delta d/T\}$.

17. The tissue localization system of claim 11 wherein the biopsy plate has a thickness T, and the holes have a diameter difference Δd greater than a needle being guided, selected for an linear accuracy A defined by:

$A = (D\Delta d)/T$;

where D is a desired penetration depth from the biopsy plate.

* * * * *